(12) United States Patent
Zhu et al.

(10) Patent No.: US 12,076,002 B2
(45) Date of Patent: Sep. 3, 2024

(54) SYSTEMS, SUTURE DEVICES, AND METHODS FOR TISSUE CLOSURE

(71) Applicant: Boston Scientific Scimed Inc., Maple Grove, MN (US)

(72) Inventors: Morgan Zhu, Somerville, MA (US); Shaun D. Comee, Fiskdale, MA (US); Peter L. Dayton, Brookline, MA (US); John T. Favreau, Spencer, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 731 days.

(21) Appl. No.: 17/010,087

(22) Filed: Sep. 2, 2020

(65) Prior Publication Data

US 2021/0068813 A1    Mar. 11, 2021

Related U.S. Application Data

(60) Provisional application No. 62/896,704, filed on Sep. 6, 2019.

(51) Int. Cl.
*A61B 17/04* (2006.01)

(52) U.S. Cl.
CPC ...... *A61B 17/0469* (2013.01); *A61B 17/0401* (2013.01); *A61B 2017/0409* (2013.01); *A61B 2017/0474* (2013.01)

(58) Field of Classification Search
CPC ............ A61B 17/0469; A61B 17/0401; A61B 2017/0409; A61B 2017/0474; A61B 17/0467; A61B 2017/0034; A61B 2017/00818; A61B 2017/0414; A61B 2017/0464; A61B 17/0466;

(Continued)

(56) References Cited

U.S. PATENT DOCUMENTS

| | | |
|---|---|---|
| 2005/0234512 A1 | 10/2005 | Nakao |
| 2007/0073321 A1 | 3/2007 | Mikkaichi et al. |
| 2018/0035997 A1 * | 2/2018 | Smith ............. A61B 17/122 |

(Continued)

FOREIGN PATENT DOCUMENTS

| | | | |
|---|---|---|---|
| EP | 1938760 A1 | 7/2008 | |
| RU | 0641546 A1 * | 9/1994 | ......... A61B 17/064 |

OTHER PUBLICATIONS

International Search Report and Written Opinion for the International Patent Application No. PCT/US2020/048997, mailed Nov. 10, 2020, 14 pages.

(Continued)

*Primary Examiner* — Brooke Labranche
*Assistant Examiner* — Nasheha Baset
(74) *Attorney, Agent, or Firm* — Seager, Tufte & Wickhem, LLP (57) ABSTRACT

The present disclosure relates generally to systems, devices, and methods for endoscopic suture termination. In some embodiments, a suture device may include an elongate member having a working channel and a suture channel, the elongate member having a proximal end and a distal end. The suture device may further include a suture extending through the suture channel, and a plurality of anchor components coupled to the suture, wherein the suture and the plurality of anchor components are deployable from the elongate member for engagement with a target tissue.

12 Claims, 12 Drawing Sheets

(58) Field of Classification Search
CPC .. A61B 2017/00867; A61B 2017/0437; A61B 2017/0454; A61B 2017/0496
See application file for complete search history.

(56) References Cited

U.S. PATENT DOCUMENTS

2020/0178956 A1  6/2020  Mitelberg et al.
2021/0068813 A1  3/2021  Zhu et al.

OTHER PUBLICATIONS

Pham, B. V., Raju, G. S., Ahmed, I., Brining, D., Chung, S., Cotton, P., . . . & Pasricha, P. J. (2006).Immediate endoscopic closure of colon perforation by using a prototype endoscopic suturing device:feasibility and outcome in a porcine model (with video). Gastrointestinal endoscopy, 64(1), 113-119.

Stavropoulos, S. N., Modayil, R., & Friedel, D. (2015). Current applications of endoscopic suturing. Worldjournal of gastrointestinal endoscopy, 7(8), 777-89.

* cited by examiner

SYSTEMS, SUTURE DEVICES, AND METHODS FOR TISSUE CLOSURE

CROSS-REFERENCE TO RELATED APPLICATION

The present application claims the benefit of priority under 35 U.S.C. § 119 to U.S. Provisional Patent Application 62/896,704, filed Sep. 6, 2019, which application is incorporated herein by reference in its entirety for all purposes.

FIELD

The present disclosure relates to the treatment of tissue defects and, more particularly, to systems, devices, and methods for tissue closure.

BACKGROUND

Surgical procedures performed within body passages, such as the digestive tract, can result in the formation of openings in tissue, for example due to the dissection of one or more lesions. Efficient closure of such openings may be hampered if the surgical procedure is performed with an instrument that is not configured to perform such closure. Therefore, various advantages may be realized by the medical devices and methods for closing openings in tissue according to the present disclosure.

SUMMARY

The present disclosure in its various embodiments relates generally to systems, suturing devices, and methods for stranded anchor deployment via an endoscope. In one or more embodiments, a suture device may include an elongate member having a working channel and a suture channel, the elongate member having a proximal end and a distal end, and a suture extending through the suture channel. The suture device may further include a plurality of anchor components coupled to the suture, wherein the suture and the plurality of anchor components are deployable from the elongate member for engagement with a target tissue. In some embodiments, the suture device may further include a delivery device extending within the suture channel, the delivery device operable to deploy an anchor component of the plurality of anchor components. In some embodiments, the delivery device may be retractable towards the proximal end of the elongate member to deploy the anchor component of the plurality of anchor components. In some embodiments, the anchor component of the plurality of anchor components may include a plurality of legs biasable from a first, collapsed configuration to a second, expanded configuration upon deployment, and an attachment device coupled to the plurality of legs, the attachment device directly connected to the suture. In some embodiments, the attachment device may be a loop surrounding the suture wire. In some embodiments, the suture device may further include an instrument within the working channel, the instrument operable to deform the attachment device to secure the anchor component to the suture wire. In some embodiments, each of the plurality of anchor components may be disposed along a suture axis within the delivery device prior to deployment. In some embodiments, the delivery device may extend beyond the distal end of the elongate member.

In one or more embodiments, an endoscopic medical device may include an elongate member having a working channel and a suture channel, the elongate member having a proximal end and a distal end, and a delivery device extending through the suture channel. The endoscopic medical device may further include a suture extending through the delivery device, and a plurality of anchor components coupled to the suture, wherein the suture and the plurality of anchor components are deployable from the delivery device for engagement with a target tissue. In some embodiments, the delivery device is extendable towards the target tissue to position a distal most anchor component of the plurality of anchor components adjacent the target tissue prior to deployment. In some embodiments, the delivery device is retractable towards the proximal end of the elongate member to deploy the distal most anchor component of the plurality of anchor components. In some embodiments, each of the anchor components of the plurality of anchor components may include a plurality of legs biasable from a first, collapsed configuration to a second, expanded configuration upon deployment. Each of the anchor components may further include an attachment device coupled to the plurality of legs, the attachment device directly connected to the suture. In some embodiments, the attachment device includes a loop surrounding the suture wire. In some embodiments, the endoscopic medical device may further include an instrument within the working channel, the instrument operable to deform the attachment device to secure the anchor component to the suture wire. In some embodiments, the delivery device may extend beyond the distal end of the elongate member.

In one or more embodiments, a method may include inserting a suture device within a patient for treatment of a target tissue, the suture device including an elongate member having a working channel and a suture channel, the elongate member having a proximal end and a distal end, a delivery device extending through the suture channel, and a plurality of anchor components coupled to a suture, wherein the plurality of anchor components and the suture are disposed within the delivery device. The method may further include deploying the suture and one or more anchor components of the plurality of anchor components for engagement with the target tissue. In some embodiments, the method may further include extending the delivery device towards the target tissue to position a distal most anchor component of the plurality of anchor components adjacent the target tissue, and retracting the delivery device towards the proximal end of the elongate member to deploy the distal most anchor component of the plurality of anchor components. In some embodiments, the method may further include biasing a plurality of legs of the distal most anchor component from a first, collapsed configuration to a second, expanded configuration upon deployment. In some embodiments, the method may further include securing the one or more anchor components of the plurality of anchor components to the suture. In some embodiments, the method may further include extending the suture through an attachment device of each of the plurality of anchor components.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

The trend in medicine is moving from laparoscopic and open surgical procedures to miniaturized, endoscopic procedures. Endoscopists can perform ever more complex non or minimally invasive procedures under direct visualization. Current endoscopes provide working channels to enable the use of dedicated instruments for such treatments, but they may not include the intrinsic capability to treat and manipulate tissue being accessed and examined. There exists a need for endoscopes which possess specific built-in treatment capabilities. Such endoscopes can facilitate both a broad range of procedural interventions that are becoming more prevalent in hospitals and can lead to the development of significantly more capable and complex scope designs.

Further, infection prevention controls in the clinical setting create a demand for single-use scopes which mitigate the risk of patient infection and associated serious adverse events. For example, currently commercial duodenoscopes often include distal tips having complex mechanical features. Such complexity can make it difficult to properly disinfect reusable scopes between procedures, which some instances can be a cause for infections sustained by patients.

Embodiments include closure devices made from superelastic material such as Nitinol, though other materials may be used, such as polymers having appropriate elastic characteristics. In some embodiments the closure devices may be delivered via an endoscope, while in other embodiments the closure devices may be delivered via a needle. The closure devices may be disposed within a lumen of the delivery device and may be delivered to the targeted tissue site in a straightened/constrained configuration. The delivery device may deploy the closure devices beyond a distal end of the device/lumen. Upon deployment, the closure devices may assume a configuration facilitating engagement of opposing segments of target tissue.

Furthermore, the disclosure may pertain to medical devices, e.g., endoscopes, gastroscopes, bronchoscopes, colonoscopes, ureteroscopes, and the like, having integrated features for acquiring, manipulating, and closing openings in target tissue. Although single-use endoscopes are described herein, it is understood that embodiments of the present disclosure may be included in reusable medical devices such as endoscopes as well. As will be further described below, embodiments herein provide suturing devices, systems, and methods including integrated mechanisms, which permit easier execution of a variety of different suturing patterns for closing tissue. For example, one type of integrated mechanism may be a set of anchors stranded continuously, e.g., serially coupled, on a suture line, wherein the suture line may be delivered through a channel of an elongate member of a suture device may. During use, each anchor may be compressed or constrained within the delivery tube and expanded or unconstrained when deployed into tissue. The anchors may be produced from a shape memory alloy or programmable polymer in order to achieve both the compressed and expanded configurations.

Figure 1A:
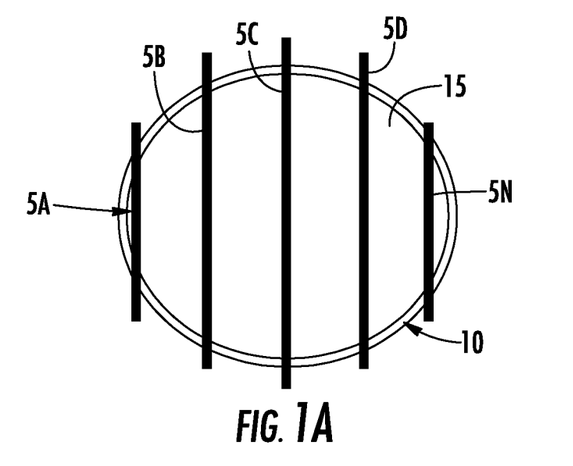
FIGS. 1A-1C demonstrate various examples of suturing patterns according to embodiments of the present disclosure.

Current endoscopic suturing may be performed according to one or more suturing patterns, which refers to the design or layout the suture traverses in a target tissue during and/or after the suturing procedure. For example, one example suturing pattern is shown in FIG. 1A, wherein each of the sutures 5A-5N may be a discreet or interrupted portion of suture wire secured about a perimeter 10 of a target tissue 15. In this case, each of the sutures 5A-5N represents a suture line which has been cut and secured in the arrangement shown. Although non-limiting, the sutures 5A-5N extend across the target tissue 15, substantially parallel to one another.

Figure 1B:
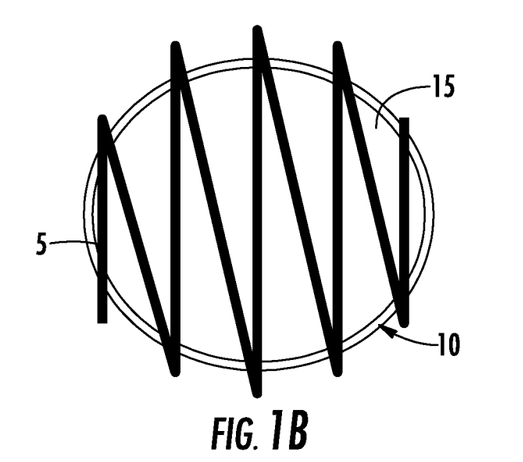

Another example suturing pattern is shown in FIG. 1B, wherein a single, continuous suture 5 may be stitched about a perimeter 10 of a target tissue 15. In this case, the suture 5 may be passed through the target tissue 15 multiple times without cutting or breaking the suture 5. Although non-limiting, the suture 5 may extend across the target tissue 15 in a zig-zag configuration.

Figure 1C:
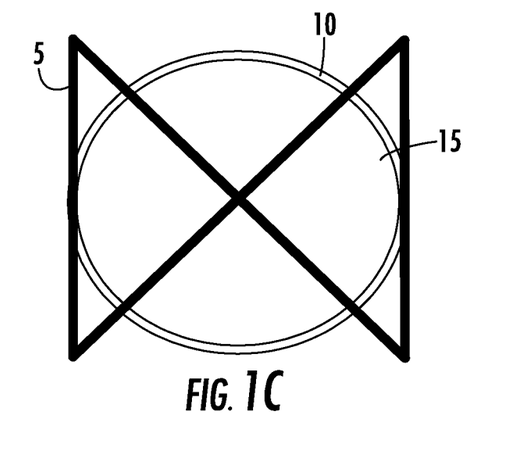

Another example suturing pattern is shown in FIG. 1C, wherein one or more sutures 5 may be threaded about a perimeter 10 of a target tissue 15, for example, in a substantially figure-eight configuration. In this case, the suture 5 may represent a single, continuous suture line or a multiple suture lines. This figure-eight suturing pattern may be particularly beneficial for treating fistulas, for example.

Figure 2A:
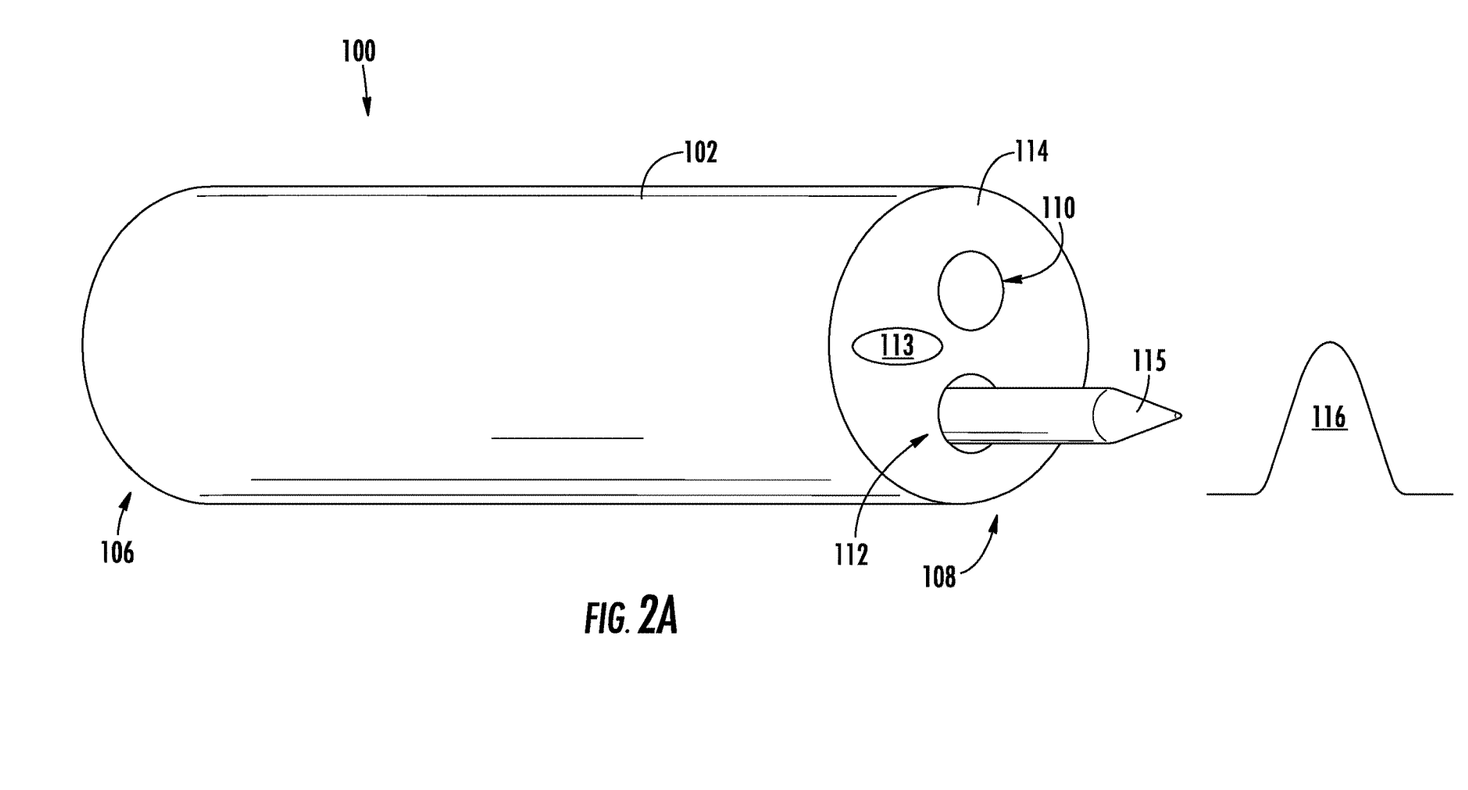
FIG. 2A is a perspective view of a system according to embodiments of the present disclosure.

Turning now to FIG. 2A, an elongate member 102 of a suturing device or system 100 according to embodiments of the disclosure will be described in greater detail. As shown, the elongate member 102 may be a hollow tube, such as a distal end of an endoscope, gastroscope, bronchoscope, colonoscope, ureteroscope, and the like. The elongate member 102 may include a proximal portion 106 opposite a distal end 108. In some embodiments, the elongate member 102 may be a flexible material, such as silicone, a thermoplastic elastomer including polyamide and polyether backbone blocks, polyurethane, etc., to allow for scope flexing. In other embodiments, the elongate member 102 may be a rigid material, such as polycarbonate, acrylonitrile butadiene styrene (ABS), etc., to provide a more direct positioning response.

As further shown, the elongate member 102 may have a working channel 110 and a suture channel 112 extending between the proximal and distal ends 106, 108. Although non-limiting, the working channel and the suture channel 112 may run generally parallel to one another within the elongate member 102. The working channel 110 may house an instrument, such as a visualization tool, a cutting tool, a manipulation tool, etc. In other embodiments, the elongate member 102 may include one or more integrated visualization devices and/or illumination devices 113 (e.g., wired or wireless cameras and/or LED's or fiber optics) positioned, for example, along a distal face 114 thereof. The suture channel 112 may include a delivery device 115 extending therethrough, wherein the delivery device 115 is operable to deploy a plurality of anchor components (not shown) into a target tissue 116. In some embodiments, the delivery device 115 may be a sheath or tube capable of moving linearly within the suture channel 112. Although a single working channel 110 and suture channel 112 are shown, it will be appreciated that more channels may be present within the elongate member 102 in other embodiments.

Figure 2B:
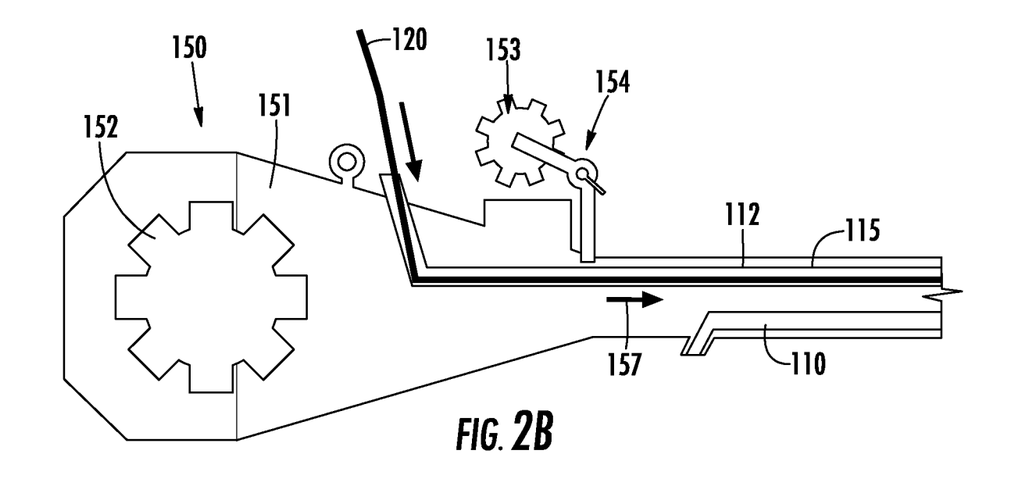
FIGS. 2B-2C are side views of a handle for operating the system of FIG. 2A according to embodiments of the present disclosure.
Figure 2C:
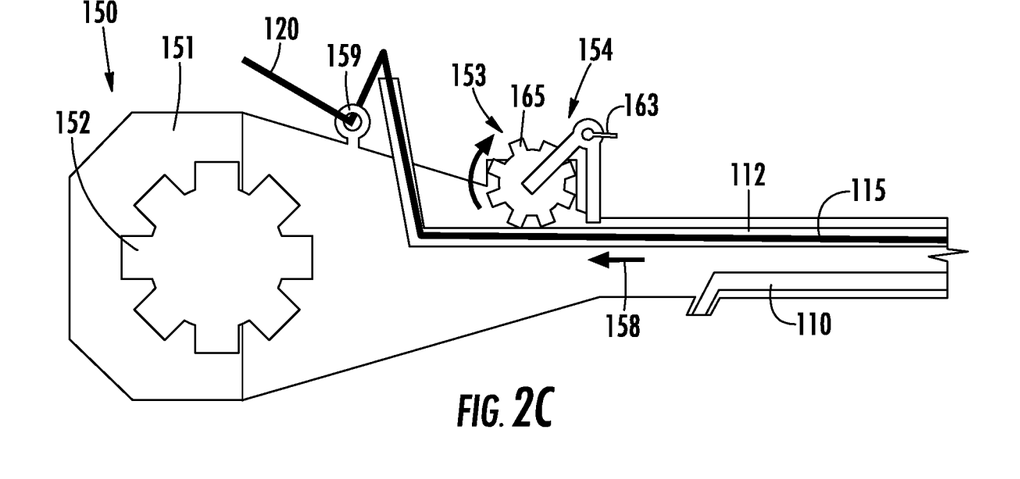

Turning now to FIGS. 2B-2C, a user interface or handle 150 for operating the system 100 according to non-limiting embodiments of the present disclosure will be described. As shown, the handle 150 may include a body 151 and one or more controls, such as a first rotation dial 152, a second rotation dial 153, and a locking hinge 154. The suture channel 112 and the working channel 110 extend through the body 151, the suture 120 and the delivery device 115 extending through the suture channel 112. During use, as shown in FIG. 2B, the locking hinge 154 may be released to allow the second rotation dial 153 to move away from the body 151, thereby permitting movement of the delivery device 115, e.g., along a direction shown by arrow 157. Although not shown in detail, the second rotation dial 153 may include one or more mechanical features operable to engage/disengage with the delivery device 115.

As shown in FIG. 2C, after suturing has been performed, the delivery device 115 may be retracted along a direction shown by arrow 158 to deploy the set of anchors (not shown) stranded on the suture line 120. To accomplish this, tension may be held on the suture 120 by an anchor 159 of the body 151 while the second rotation dial 153 engages the delivery device 115. Rotation of the second rotation dial 153 (e.g., in a direction shown by arrow 161) moves the delivery device 115 axially within the suture channel 112. In some embodiments, the locking hinge 154 may allow for fine advancement of the delivery device 115. For example, the locking hinge 154 may include a lever 163 and one or more arresting features (not shown) operable with mechanical detents 165 of the second rotation dial 153 for the purpose of dividing rotation of the second rotation dial into discrete increments. Embodiments herein are not limited in this context.

Figure 3:
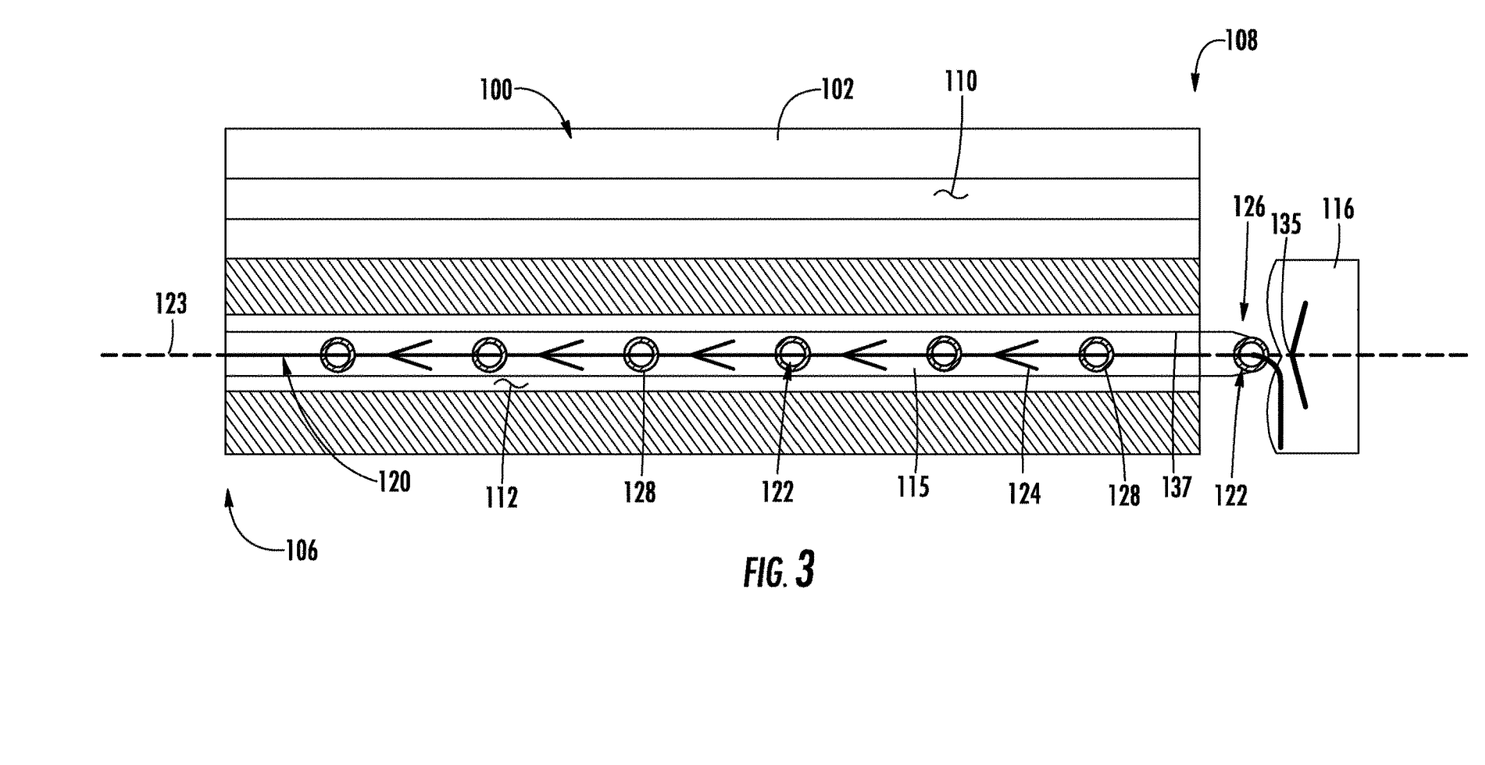
FIG. 3 is a side cross-sectional view of the system of FIG. 2A according to embodiments of the present disclosure
Figure 4A:
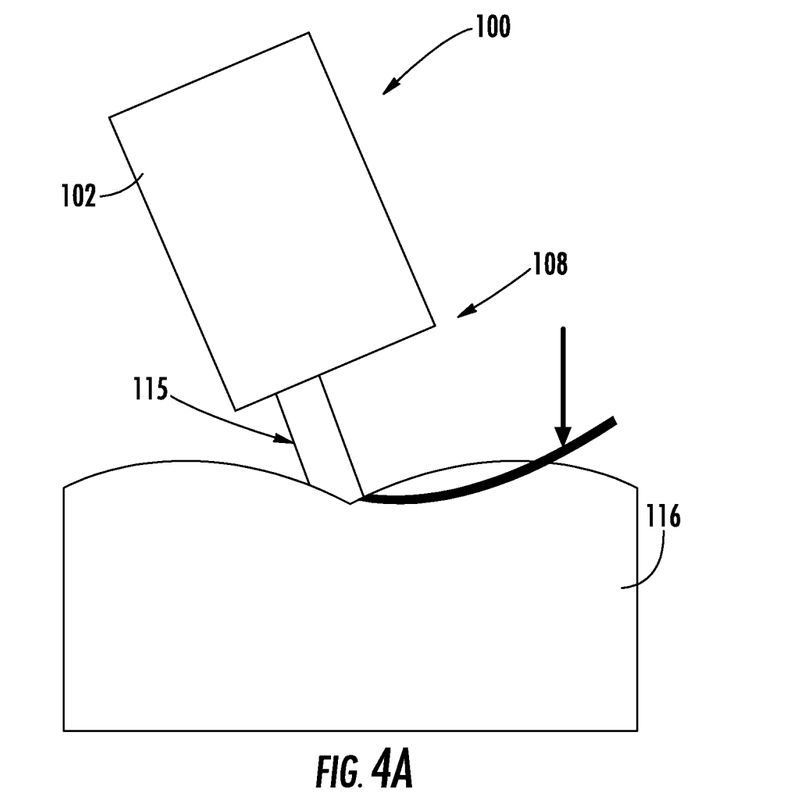
FIG. 4A is a side view of the system of FIG. 2A during use according to embodiments of the present disclosure.
Figure 4B:
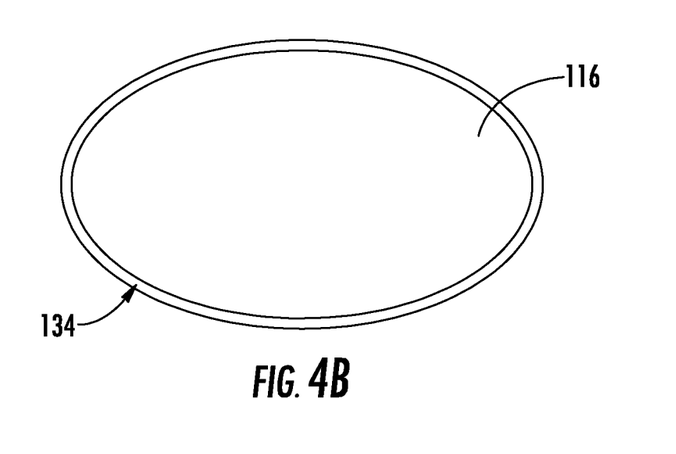
FIG. 4B demonstrates a suturing pattern resulting from the system of FIG. 4A according to embodiments of the present disclosure.

As shown in FIG. 3, the system 100 may further include a suture 120 extending through the suture channel 112. More specifically, the suture 120 may extend through an interior of the delivery device 115 for deploying one or more anchor components 122 into the target tissue 116. The delivery device 115 may extend beyond the distal end 108 of the elongate member 102 to deploy the anchor components 122. In some embodiments, each anchor component 122 may include a plurality of legs 124 biasable from a first, collapsed configuration when positioned within the delivery device 115, to a second, expanded configuration upon deployment from a distal end 126 of the delivery device 115. For example, the plurality of legs 124 may be coupled at a connection point 135 disposed along a suture axis 123. Each of the plurality of legs 124 may include a fixed end and a free end, wherein the free ends extend towards the distal end 108 of the elongate member 102. Once released from the distal end 126 of the delivery device 115, the plurality of legs 124 may pivot about the connection point 135, swinging away from the suture axis 123. An interior surface 137 of the delivery device 115 may physically constrain the plurality of legs 124 to maintain the anchor components 122 in the collapsed configuration prior to deployment.

During deployment, the plurality of legs 124 of the anchor components 122 may initially act as a stylet sharp, piercing the target tissue 116 when deployed. In some embodiments, the plurality of legs 124 may extend at least partially beyond the distal end 126 of the delivery device 115 to enable the plurality of legs 124 to be the initial point of engagement with the target tissue 116. In other embodiments, the distal end 126 of the delivery device 115 may initially penetrate the target tissue 116 using, for example, a needle or electrocautery. In yet other embodiments, the distal end 126 of the delivery device 115 may abut or engage the target tissue 116 without penetration. The anchor components 122 may then be deployed into the target tissue 116. Although non-limiting, the anchor components 122 may be produced from a shape memory alloy or programmable polymer in order to achieve both the compressed and expanded configurations.

As further shown, the anchor components 122 may include an attachment device 128 coupled to the plurality of legs 124, wherein the attachment device 128 is further connected to the suture 120. For example, the attachment device 128 may be a loop extending round the suture 120. The loop may be sized to allow the suture 120 to pass freely therethrough. As further described below, the attachment device 128 may be deformed or crimped to secure the attachment device 128 to the suture 120 after the plurality of legs 124 engage the target tissue 116.

Turning now to FIGS. 4A-9B, a non-limiting example demonstrating operation of the system 100 will be described in greater detail. It will be appreciated that FIGS. 4A, 5A, 6A, 7A, 8A, and 9A depict side views of the system 100 during use, while FIGS. 4B, 5B, 6B, 7B, 8B, and 9B depict corresponding suturing patterns that may be achieved as a result. As first shown in FIGS. 4A-4B, the elongate member 102 may be brought into position proximate the target tissue 116, which may correspond to an area of tissue containing a tear, defect, or opening to be sutured by the suture 120. The delivery device 115 may extend from the distal end 108 of the elongate member 102, where it is brought into contact or positioned directly adjacent the target tissue 116, for example, along a perimeter 134 surrounding the target tissue 116. Although non-limiting, the delivery device 115 may be relatively upright (i.e., perpendicular) with respect to the target tissue 116 to enable better delivery of the anchor components 122.

Figure 5A:
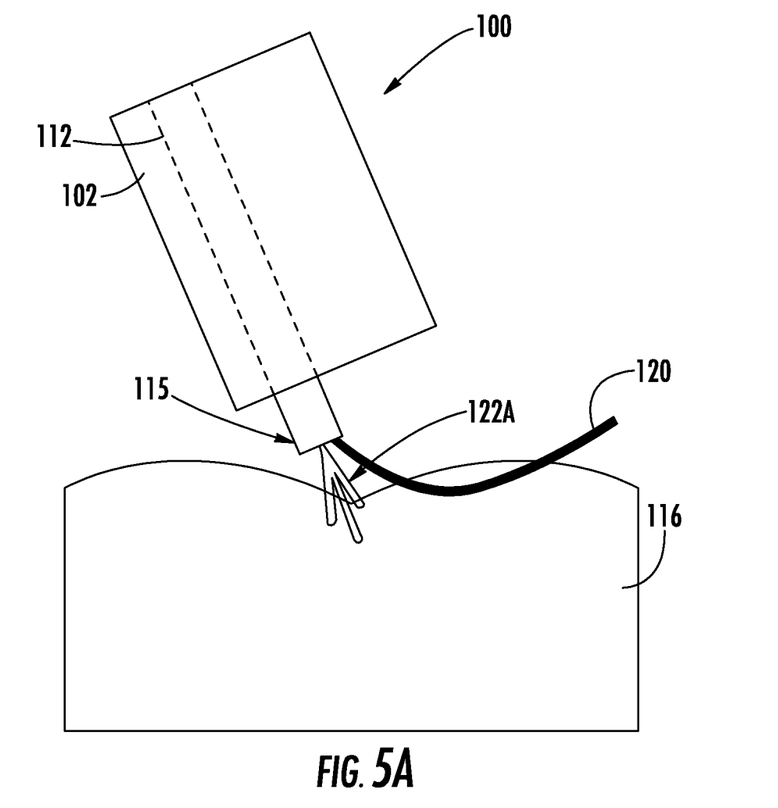
FIG. 5A is a side view of the system of FIG. 2A during use according to embodiments of the present disclosure.
Figure 5B:
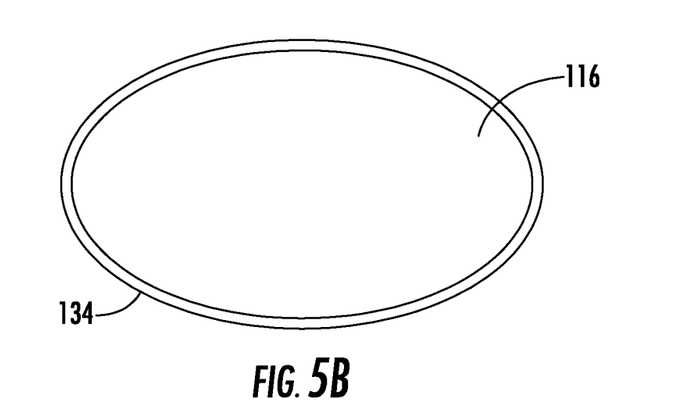
FIG. 5B demonstrates a suturing pattern resulting from the system of FIG. 5A according to embodiments of the present disclosure.
Figure 6A:
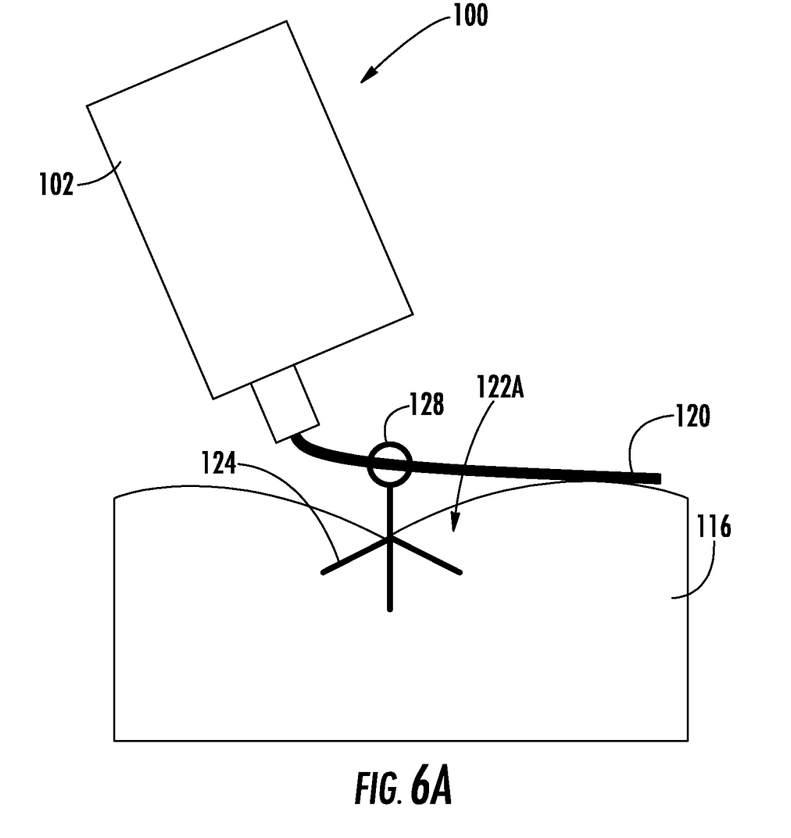
FIG. 6A is a side view of the system of FIG. 2A during use according to embodiments of the present disclosure.
Figure 6B:
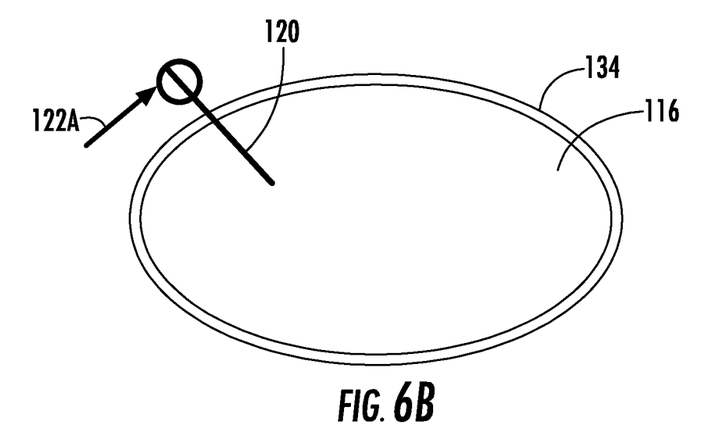
FIG. 6B demonstrates a suturing pattern resulting from the system of FIG. 6A according to embodiments of the present disclosure.
Figure 7A:
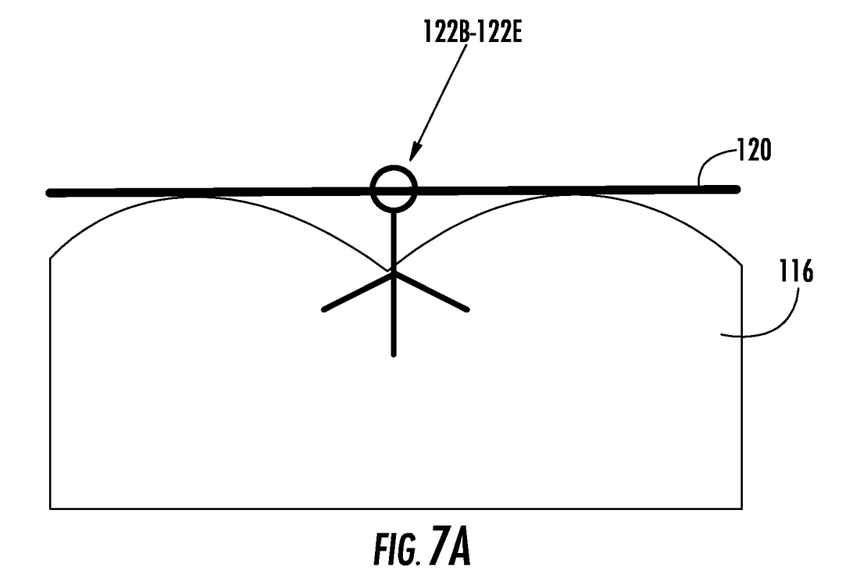
FIG. 7A is a side view of the system of FIG. 2A during use according to embodiments of the present disclosure.
Figure 7B:
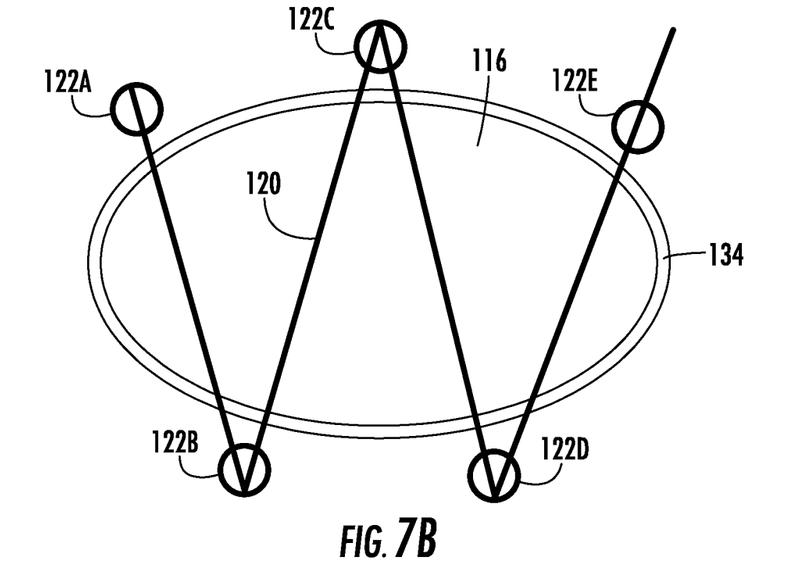
FIG. 7B demonstrates a suturing pattern resulting from the system of FIG. 7A according to embodiments of the present disclosure.

Next, as shown in FIGS. 5A-5B, a first, distal most anchoring component 122A may be deployed from the delivery device 115 as the delivery device 115 traverses the perimeter 134. In some embodiments, the delivery device 115 is retracted into the suture channel 112 of the elongate member 102. As shown, the suture 120 may extend adjacent the first anchoring component 122A, extending both inside and outside of the delivery device 115. The elongate member 102 may continue to move along the perimeter 134, as shown in FIGS. 6A-6B, allowing the first anchoring component 122A to fully deploy from the delivery device 115. More specifically, the plurality of legs 124 are expanded to secure the first anchoring component 122A in place within the target tissue 116. Furthermore, the suture 120 may extend through the opening of the attachment device 128. As shown in FIGS. 7A-7B, one or more additional anchoring components 122B-122E may be further deployed at desired positions in or around the target tissue 116. In the non-limiting embodiment shown, the suture 120 may be patterned in a 'W' configuration around the perimeter 134 of the target tissue 116. However, it will be appreciated that many alternative suture and anchoring component configurations may be possible within the scope of the present disclosure.

Figure 8A:
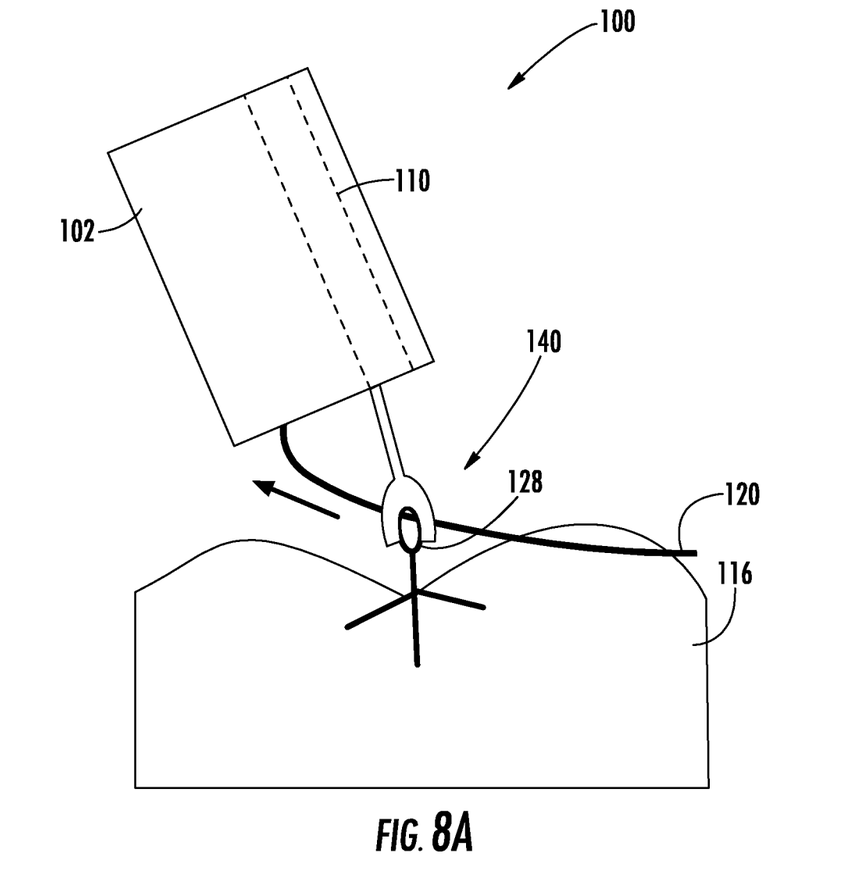
FIG. 8A is a side view of the system of FIG. 2A during use according to embodiments of the present disclosure.
Figure 8B:
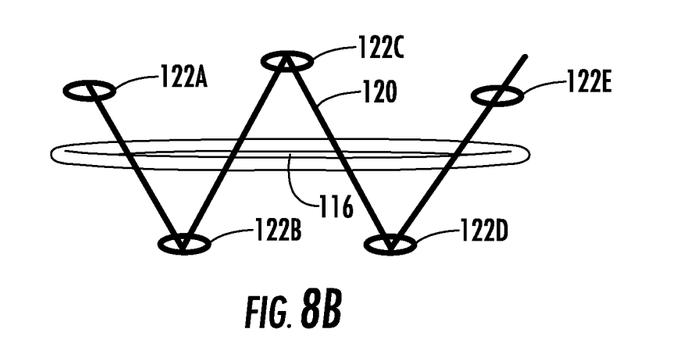
FIG. 8B demonstrates a suturing pattern resulting from the system of FIG. 8A according to embodiments of the present disclosure.
Figure 9A:
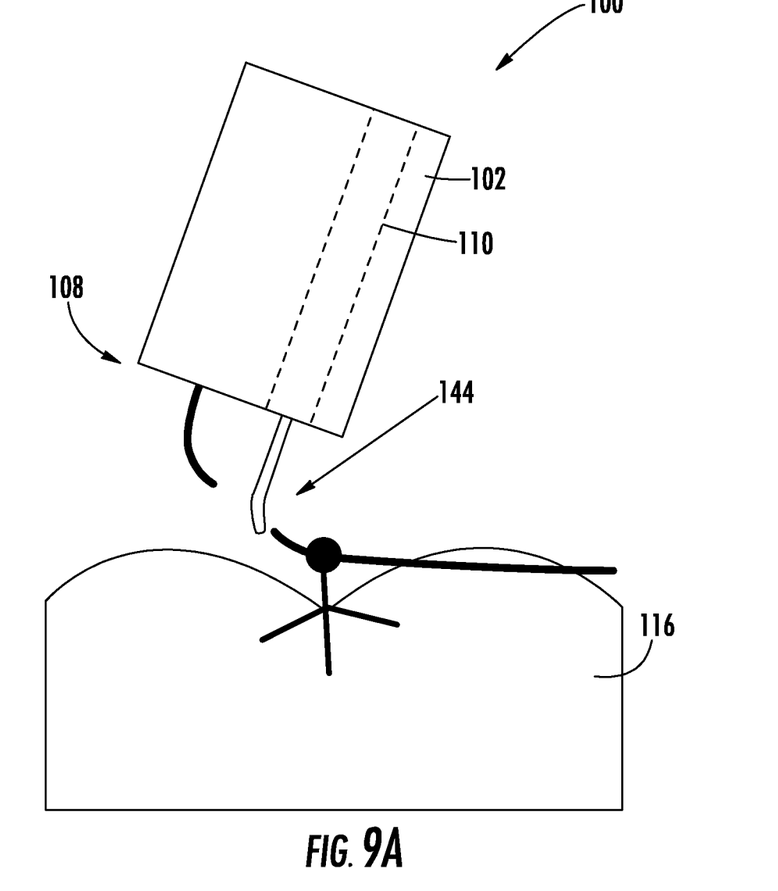
FIG. 9A is a side view of the system of FIG. 2A during use according to embodiments of the present disclosure.
Figure 9B:
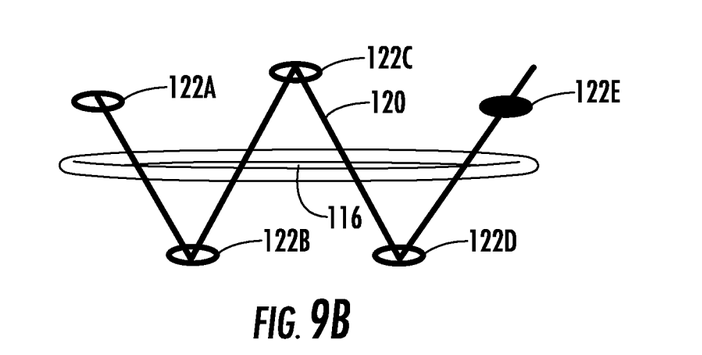
FIG. 9B demonstrates a suturing pattern resulting from the system of FIG. 9A according to embodiments of the present disclosure.
Figure 10A:
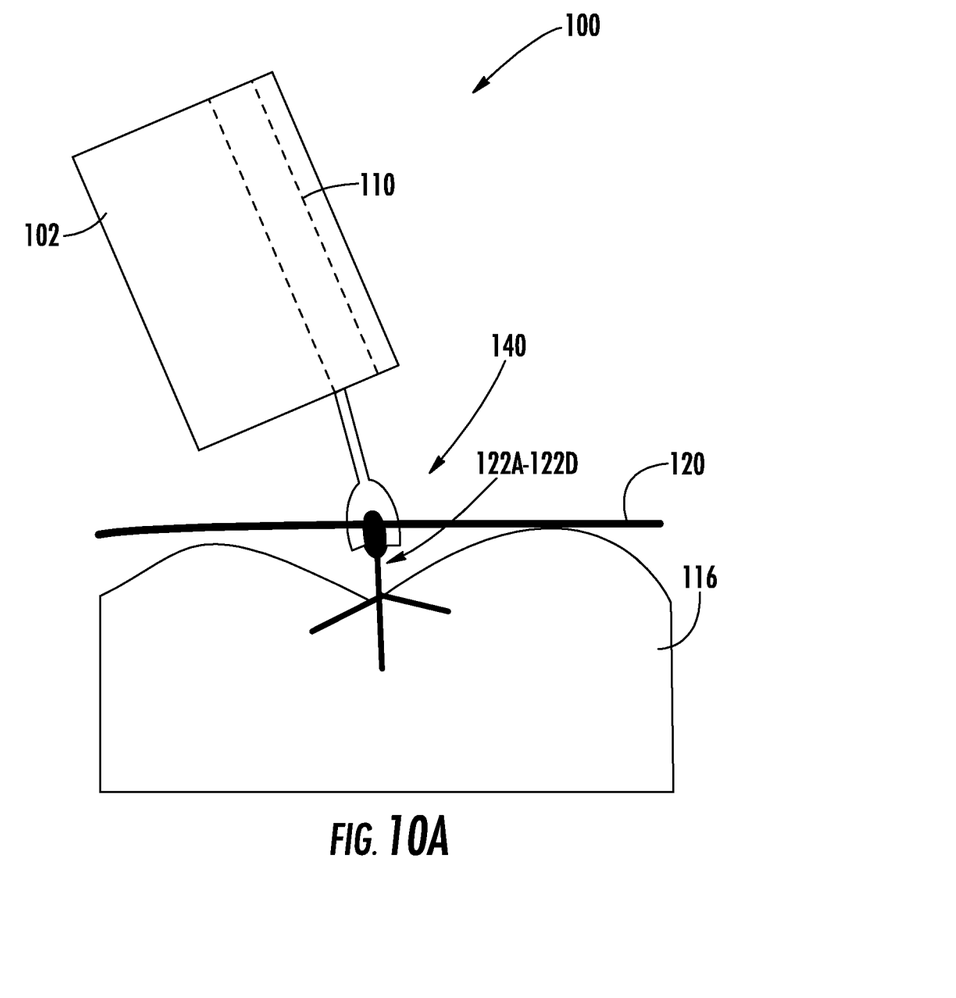
FIG. 10A is a side view of the system of FIG. 2A during use according to embodiments of the present disclosure.
Figure 10B:
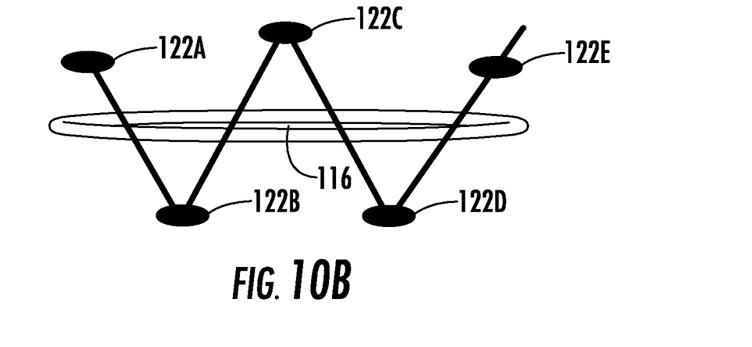
FIG. 10B demonstrates a suturing pattern resulting from the system of FIG. 10A according to embodiments of the present disclosure.

Next, as shown in FIGS. 8A-8B, a first tool 140 may extend from the working channel 110 of the elongate member 102 and engage any of the anchoring components 122A-122E. For example, the first tool 140 may be a crimping tool operable to deform the attachment device 128 around the suture 120 to prevent the suture 120 from moving relative to the attachment device 128. In some embodiments, once the final anchoring component (e.g., anchoring component 122E) has been deployed, the suture 120 may be tightened to close the defect of the target tissue 116. Anchoring component 122E may then be crimped and the suture 120 cut, as shown in FIG. 9A-9B. In some embodiments, a second tool 144 (e.g., a cutting tool) may be inserted through the working channel 110 to sever the suture 120 in an area between the anchoring component 122E and the distal end 108 of the elongate member 102. Finally, as shown in FIGS. 10A-10B, the first tool 140 may again be extended through the working channel 110 to crimp one or more of anchoring components 122A-122D. In other embodiments, some or all of the anchoring components 122A-122E may be crimped prior to the cutting of the suture 120. In other words, it may be more efficient to crimp all the anchoring components 122A-122E before removing the first tool 140 from the working channel 110 and inserting the second tool 144. In yet other embodiments, more than one working channel may be present, allowing both the first and second tools 140, 144 to be used sequentially.

Figure 11:
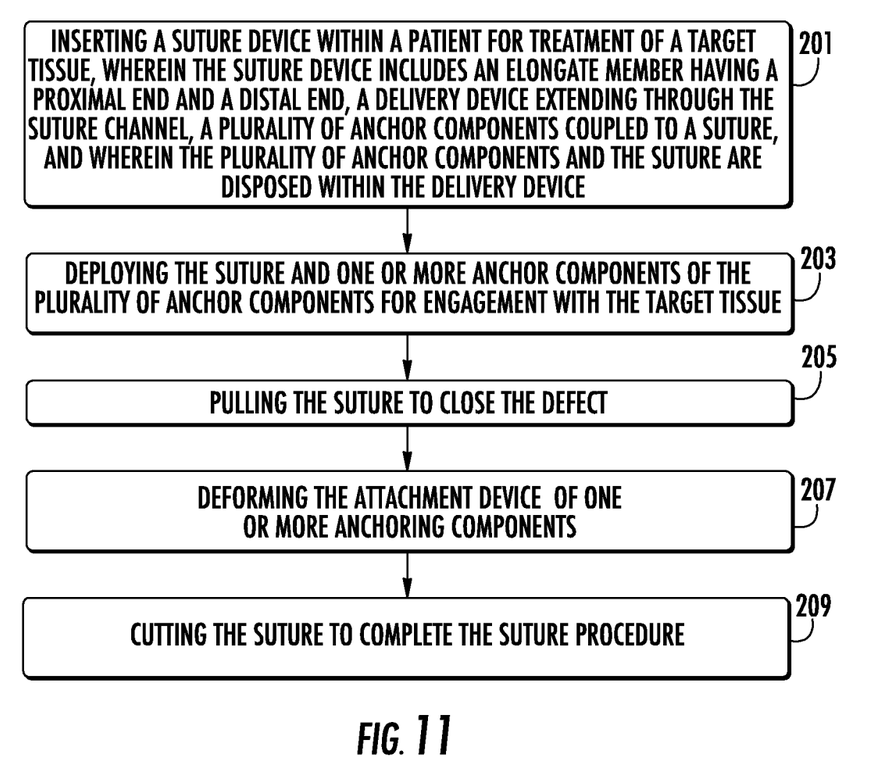
FIG. 11 is a flow diagram of a method according to embodiments of the present disclosure.

FIG. 11 is a flow diagram of a method 200 according to embodiments of the present disclosure. At block 201, the method 200 may include inserting a suture device within a patient for treatment of a target tissue, wherein the suture device includes an elongate member having a working channel and a suture channel, the elongate member having a proximal end and a distal end, a delivery device extending through the suture channel, a plurality of anchor components coupled to a suture, and wherein the plurality of anchor components and the suture are disposed within the delivery device.

At block 203, the method 200 may include deploying the suture and one or more anchor components of the plurality of anchor components for engagement with the target tissue. In some embodiments, the delivery device may be extended towards the target tissue to position a distal most anchor component of the plurality of anchor components adjacent the target tissue. The delivery device may then be retracted towards the proximal end of the elongate member to deploy the distal most anchor component of the plurality of anchor components.

In some embodiments, the anchoring components may each include a plurality of legs connected to an attachment device. As the anchoring components are deployed from the delivery device and into the target tissue, the plurality of legs may be biased from a first, collapsed configuration to a second, expanded configuration within the target tissue. In some embodiments, the attachment device may connect the anchor components to the suture. In some embodiments, the suture may extend through the attachment device, for example, in the case the attachment device includes a loop or passageway.

At block 205, the method 200 may optionally include pulling the suture to close the defect. In some embodiments, the target tissue may be cinched inward to close an opening or tear. At block 207, the method 200 may optionally include deforming the attachment device of one or more anchoring components. In some embodiments, a first tool, such as a crimper, may be disposed within the working channel of the elongate member. The crimper may extend from the distal end of the elongate member, and crimp the attachment device to secure the anchoring component in place along the suture wire.

At block 209, the method 200 may optionally include cutting the suture to complete the suture procedure. In some embodiments, a second tool, such as a knife or blade may extend from the working channel to sever the suture between one of the anchoring components and the elongate member. With the suture secured by the anchoring components, the suture will not unravel.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Although non-limiting, as used herein with respect to the elongate member(s), the term "proximal portion" may refer to a portion of the endoscope closest to a handle or user interface of the system, while the term "distal end" may refer to a portion of the endoscope farthest from the handle or user interface of the system.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 200 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A suture device, comprising:
   an elongate member having a working channel and a suture channel, the elongate member having a proximal end and a distal end,
   wherein the suture channel is a lumen extending longitudinally throughout the elongate member;
   a suture extending through the suture channel; and
   a plurality of anchor components coupled to the suture such that each of the plurality of anchor components is disposed along a suture axis within a delivery device prior to deployment, wherein the suture and the plurality of anchor components are deployable from the elongate member for engagement with a target tissue,
   wherein at least one anchor component of the plurality of anchor components comprises:
      a plurality of legs biasable from a first, collapsed configuration to a second, expanded configuration upon deployment; and
      an attachment device coupled to the plurality of legs and connected to the suture.

2. The suture device of claim 1, further comprising the delivery device extending within the suture channel, the delivery device operable to deploy an anchor component of the plurality of anchor components.

3. The suture device of claim 2, wherein the delivery device is retractable towards the proximal end of the elongate member to deploy the anchor component of the plurality of anchor components.

4. The suture device of claim 2, wherein the attachment device includes a loop surrounding the suture.

5. The suture device of claim 4, further comprising an instrument within the working channel, the instrument operable to deform the loop to secure the anchor component to the suture.

6. The suture device of claim 2, wherein the delivery device extends beyond the distal end of the elongate member.

7. An endoscopic medical device, comprising:
- an elongate member having a working channel and a suture channel, the elongate member having a proximal end and a distal end,
- wherein the suture channel is a lumen extending longitudinally throughout the elongate member;
- a delivery device extending through the suture channel; a suture extending through the delivery device; and
- a plurality of anchor components coupled to the suture such that each of the plurality of anchor components is disposed along a suture axis within the delivery device prior to deployment, wherein the suture and the plurality of anchor components are deployable from the delivery device for engagement with a target tissue,
- wherein each of the anchor components of the plurality of anchor components comprises:
  - a plurality of legs biasable from a first, collapsed configuration to a second, expanded configuration upon deployment; and
  - an attachment device coupled to the plurality of legs and connected to the suture.

8. The endoscopic medical device of claim 7, wherein the delivery device is extendable towards the target tissue to position a distal most anchor component of the plurality of anchor components adjacent the target tissue.

9. The endoscopic medical device of claim 8, wherein the delivery device is retractable towards the proximal end of the elongate member to deploy the distal most anchor component of the plurality of anchor components.

10. The endoscopic medical device of claim 9, wherein the attachment device includes a loop surrounding the suture.

11. The endoscopic medical device of claim 10, further comprising an instrument within the working channel, the instrument operable to deform the loop to secure the anchor component to the suture.

12. The endoscopic medical device of claim 7, wherein the delivery device extends beyond the distal end of the elongate member.

* * * * *